Figure 2:
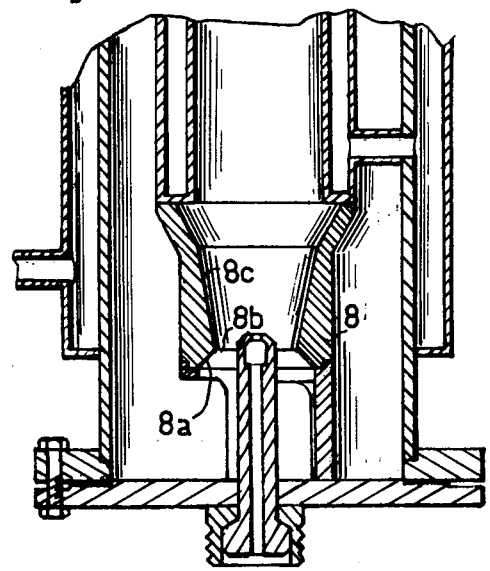

United States Patent [19]

Chelle

[11] 4,204,042
[45] May 20, 1980

[54] METHOD OF GASIFYING AND AGITATING A FERMENTATION CULTURE

[75] Inventor: René Chelle, Toulouse, France

[73] Assignee: Societe Anonyme S.E.T.R.I.C., Toulouse, France

[21] Appl. No.: 876,545

[22] Filed: Feb. 9, 1978

[30] Foreign Application Priority Data

Feb. 23, 1977 [FR] France .............................. 77 05872

[51] Int. Cl.$^2$ .............................................. C12N 1/20
[52] U.S. Cl. .................................... 435/253; 435/243; 435/313; 435/314; 435/818; 435/837
[58] Field of Search ...................... 195/109, 104, 108

[56] References Cited

U.S. PATENT DOCUMENTS

| 3,002,894 | 10/1961 | Rungaldier et al. | 195/109 X |
| 3,384,553 | 5/1968 | Caslavsky et al. | 195/109 X |
| 3,732,148 | 5/1973 | Franckowiak et al. | 195/109 |
| 3,857,757 | 12/1974 | Herrick et al. | 195/109 |
| 3,929,582 | 12/1975 | Kellner | 195/109 X |
| 3,957,585 | 5/1976 | Malick | 195/109 |
| 3,982,998 | 9/1976 | Hitzman et al. | 195/109 X |

Primary Examiner—Alvin E. Tanenholtz
Assistant Examiner—Robert J. Warden
Attorney, Agent, or Firm—Shlesinger, Arkwright, Garvey & Dinsmore

[57] ABSTRACT

The invention relates to a method of and an apparatus for enabling a micro-organism culture to be gasified and agitated so as to accelerate its growth. The culture is contained in a fermenter which comprises two containers $C_1$ and $C_2$ which communicate with one another in their upper and lower regions. The method consists of injecting sterile air in the form of bubbles discontinuously at the base of one $C_1$ of the containers with injection periods of predetermined length alternating with non-injection periods at a predetermined frequency. This sequential infeed of air produces a surging or pulsating effect in the culture which, for a given consumption of air, very considerably increases the density of micro-organism achieved at the end of a given period of time. The invention is applicable to the cultivation of all aerobic micro-organisms:cells, fungi, bacteria, etc.

7 Claims, 12 Drawing Figures

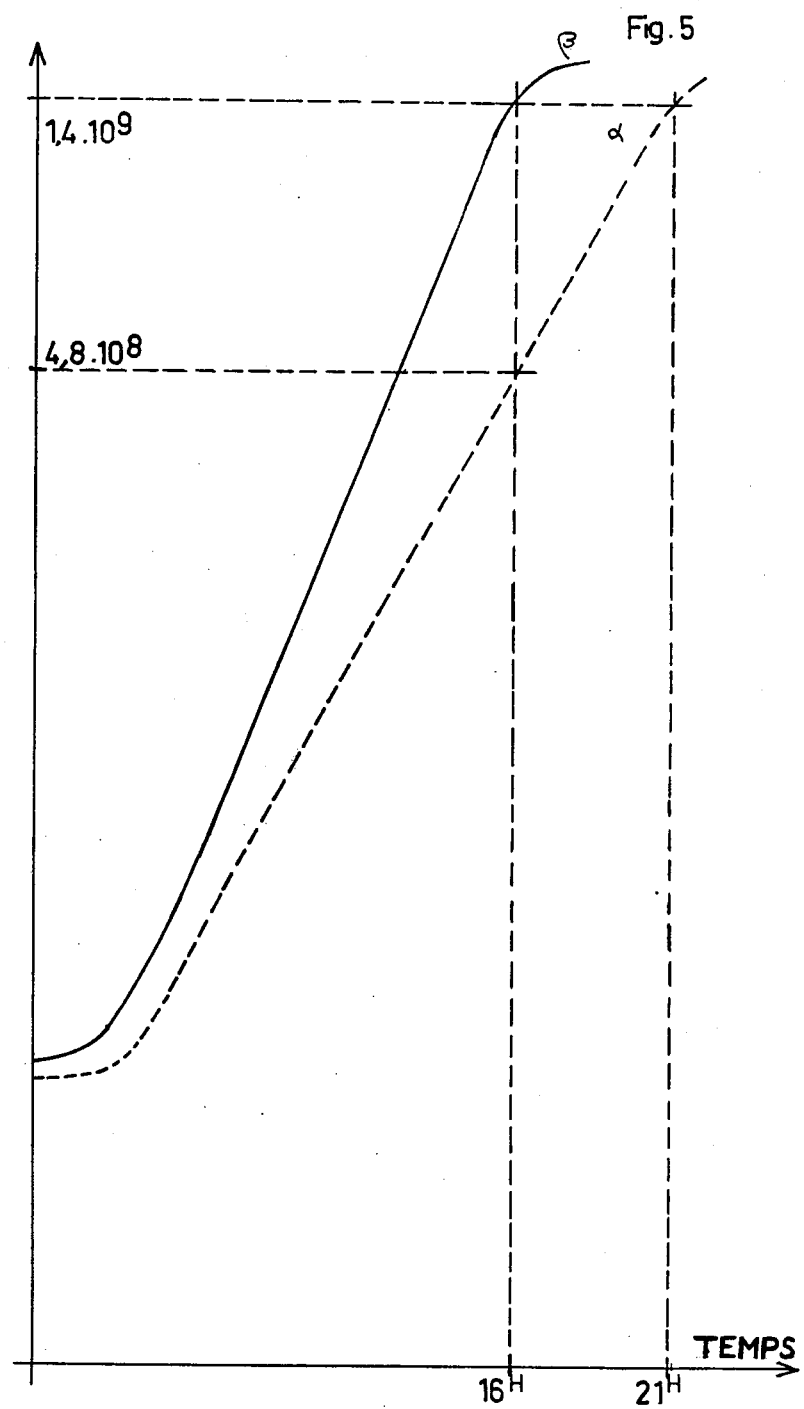

METHOD OF GASIFYING AND AGITATING A FERMENTATION CULTURE

BACKGROUND OF THE INVENTION

The present invention relates to a method of gasifying and agitating a micro-organism culture which enables its growth to be accelerated. It also relates to a fermenting apparatus for putting this method into practice.

It is known that there are at the present time two chief methods for homogenising a culture medium and for increasing the rate of dissolution of air with a view to growing aerobic micro-organisms (cells, fungi, bacteria, etc). One of these is mechanical and consists in agitating the medium mechanically while injecting into it the sterile air needed for the development of the micro-organisms, while the other referred to as the "airlift" method, consists in imparting motion to the medium directly using bubbles of air which are fed continuously at the base of the fermenter.

The first method has a number of disadvantages. Firstly it calls for fermenters whose structure is far more complicated since they include a mechanical assembly with a drive motor, agitator members, sealing glands, etc. In addition such fermenters are ill suited to continuous operation because of the sterility problems which arise as a result of the structural complexity of the fermenter which must include rotary joints and so on.

The airlift method referred to above can be put into effect with far simpler apparatus which is able to operate continuously and which does not raise the sterility problems which exist with mechanical methods. However, a major disadvantage of methods of this kind lies in the consumption of air which they involve, which is very much greater than with mechanical methods. To give an example, at a comparable rate of growth, in cases where mechanical methods would call for a consumption of 1 v.v.m (volume of air per volume of culture per minute), the airlift method calls for a consumption which may be of the order of 3 v.v.m. If this consumption is reduced, the medium is not adequately agitated and the rate of growth of the micro-organisms falls off sharply. However, the air which is admitted into a fermenter is an expensive commodity since it must have been very thoroughly sterilized beforehand to prevent or minimise any contamination of the medium. Thus, in airlift methods the cost of a culture of given density or microbial concentration depends in essence on the initial seeding cost, on the cost of the nutrient medium, and on the cost of the energy consumed and it is this latter, which is proportional to the consumption of sterile air, which is generally the dominant factor.

It is an object of the invention considerably to reduce the importance of the factor mentioned above and to this end it aims to provide an improved method of gasifying and agitating a micro-organism culture which also benefits from the advantages of the airlift method.

In other words, an object of the invention is, in any given application, either to increase the density of micro-organisms achieved for a given air consumption, or to reduce considerably the consumption of air required to obtain a given density, or again to have a favourable effect on both these factors in order to allow micro-organisms to be produced under the optimum conditions in any set of practical circumstances.

In a similar fashion to the airlift method, the method to which the invention relates calls for the culture to be placed in a fermenter comprising at least two containers which communicate with one another in their upper and lower regions. The method according to the invention consists in injecting substantially sterile air in the form of bubbles discontinuously at the base of one of the containers, with injection periods of predetermined length and non-injection periods alternating at a predetermined frequency, thus having a surging or pulsating effect on the culture in the two containers, a general flow between the containers taking place through the intercommunications between them.

As will better be appreciated at a later stage, this surging or pulsating effect on the culture is produced by the alternating infeed of air and considerably increases the movement in the culture and its growth. For example, with an identical mean consumption of the substantially sterile air, it is found that the method of the invention on the one hand enables the length of the latency phase i.e. the initial phase in the course of which the rate of growth is very slow to be reduced in comparison with the conventional airlift method, and on the other hand enables the rate of growth during development to be very considerably increased, with the result that, at the end of a given period of operating the method, the micro-organism density in the culture is considerably greater than the density which would have been achieved under the same operating conditions with the conventional method, while the consumption of air will have been the same. By way of illustration, the ratio between the densities may be of the order of 3:1.

In practice, the frequency of the injections of air will be equal to at least one per minute, with the aim of producing an effective surge effect. Furthermore, experiments have shown that good results can be obtained with non-injection periods whose length is of the order of 0.5 to 10 times that of the injection periods.

In a first manner of putting the method into practice, the injection frequency and the length of the injection periods are constant and are present to suit the oxygen requirements of the micro-organisms and the degree of agitation required. The settings may be arrived at by conducting preliminary tests with the strain of micro-organism concerned.

In another manner of implementation, the frequency of injection and the length of the injection periods are variable and are controlled at all times by sensors which are associated with the culture to allow its state to be detected, with a view to meeting the requirements of the organisms in the optimum fashion at each stage of growth.

The invention also relates to fermentation apparatus for putting into effect the method described above. This apparatus is of the airlift kind and comprises two containers which communicate with one another in their upper and lower regions, and an air injector which opens into one of them: the latter may be formed by a vertical column arranged in the other container, which latter is itself formed by a vertical column of larger diameter. The air injector is advantageously associated with sequential air supply means which are adapted to supply substantially sterile air for periods of predetermined length at a predetermined frequency.

The two containers preferably communicate in their lower regions via a venturi member which contains a constriction, the air injector opening into the first mentioned container close to this constriction in order, during the injection periods, to produce an effect whereby the culture is drawn from the other container into the first container. The surge effect is thereby considerably increased.

Figure 1:
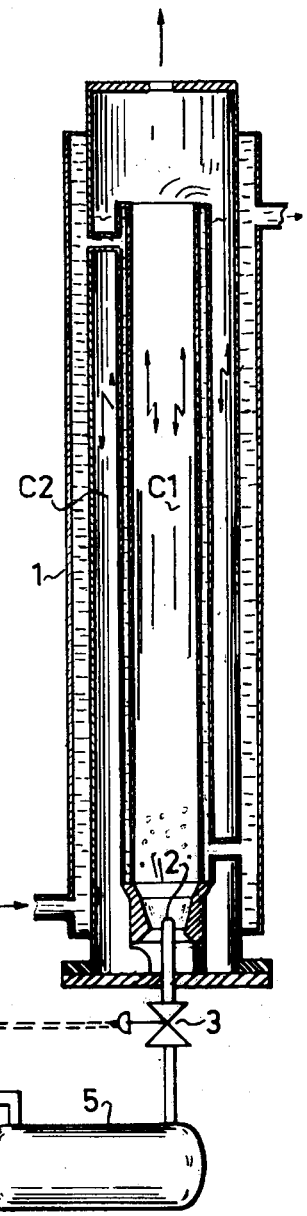
Figure 3:
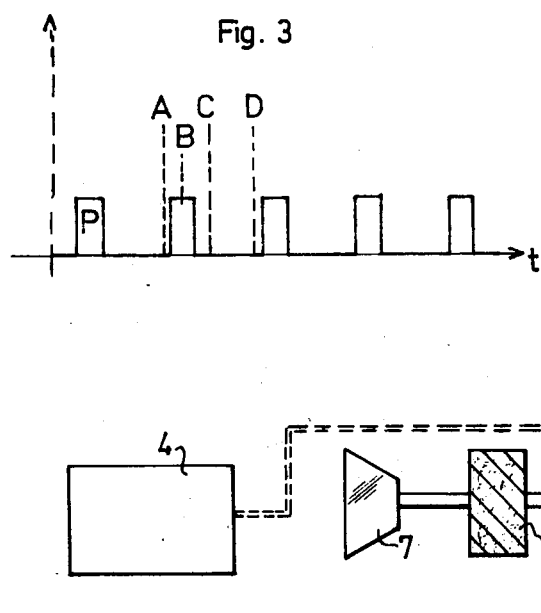
Figure 6:
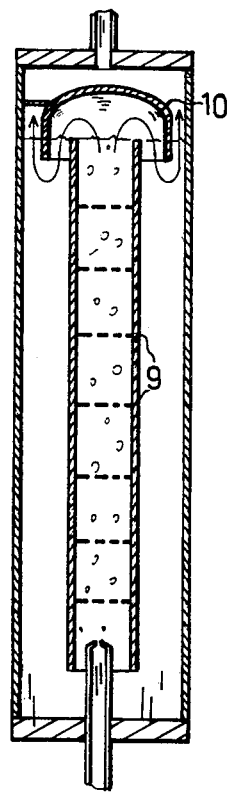
Figure 7:
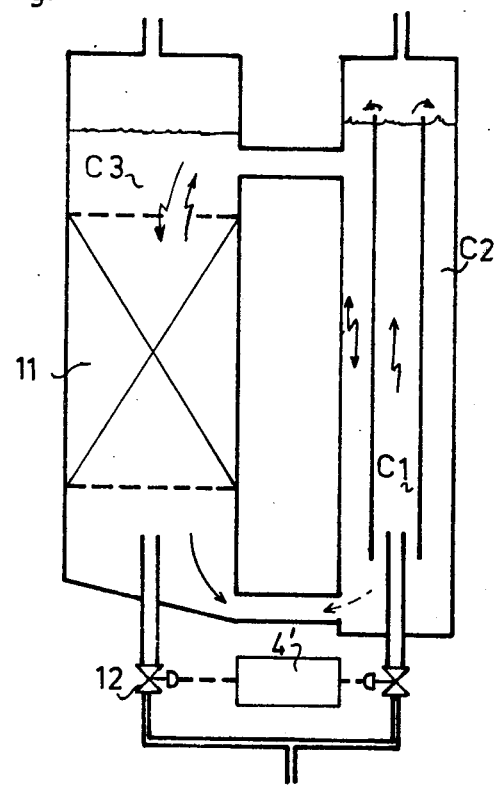
Figure 8A:
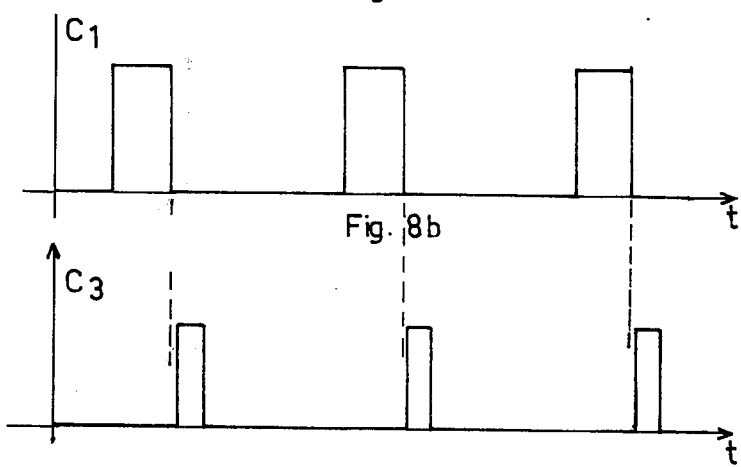
Figure 8B:
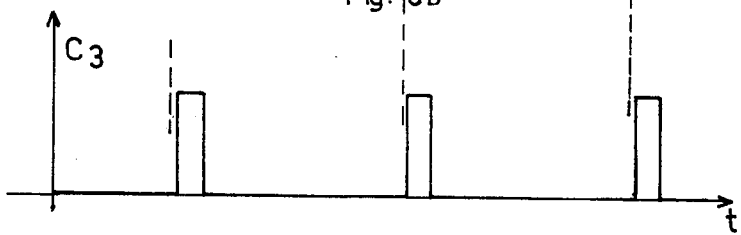

In order that the invention may be more clearly understood, reference will now be made to the accompanying drawings, which show some embodiments of apparatus according thereto by way of example, and in which:

FIG. 1 is a schematic view of a fermenting apparatus according to the invention, FIG. 2 is a cross-sectional detail view of part of this apparatus in a vertical axial plane, FIG. 3 is a diagram as a function of time of the operation of the said apparatus, FIGS. 4a, 4b, 4c and 4d are diagrams illustrating the pulsatory or surging movements of the culture in the course of an air supply cycle, FIG. 5 shows curves against a logarithmic scale for the concentration of micro-organisms as a function of time in the case of a conventional airlift method (curve $\alpha$) and in the case of the method according to the invention (curve $\beta$), FIGS. 6 and 7 are diagrams of other embodiments of apparatus and FIGS. 8a and 8b are diagrams as a function of time illustrating the operation of the apparatus shown in FIG. 7.

Referring now to the drawings, the fermenting apparatus which is shown by way of example in FIGS. 1 and 2 comprises a fermenter 1 made up of a first vertical column $C_1$ and a second vertical column $C_2$ which surrounds the first, an air injector 2 which opens at the base of column $C_1$, an electrically operated valve 3 which supplies the injector 2 with air sequentially and which is controlled by electrical means for sequential control which are indicated at 4, a buffer tank 5, an air sterlising filter 6, and a compressor 7. The buffer tank 5, which is situated between the compressor and the valve downstream of the filter, acts as protection for the filter.

In the embodiment shown, the two containers $C_1$ and $C_2$ are surrounded by envelopes which, in the conventional fashion, allow a flow of thermostatic fluid to be provided for.

In its lower region column $C_1$ communicates with column $C_2$ via a neck 8 (FIG. 2) which is adapted to produce a venturi effect in the periods when air is injected and to cause liquid to be drawn from column $C_2$ into column $C_1$. To this end, the neck 8 has a convergent portion 8a, a constriction 8b and a divergent portion 8c, the air injector opening into column $C_1$ near the constriction 8b. In this embodiment column $C_1$ rests on the floor of column $C_2$ and contains, in its lower region, underneath the neck 8, wide openings for the passage of the liquid.

In addition, column $C_1$ is open at the top and is thus able to communicate with column $C_2$ as a result of the overflow of liquid.

The means 4 for controlling the valve 3 emit electrical pulses which cause the valve to open and close alternately at a predetermined frequency. The diagram in FIG. 3 shows the amounts of substantially sterile air injected as a function of time. The length of the injection periods P may vary between 0.5 and approximately 7 to 8 seconds, the frequency of injection being equal to at least four injections per minute. The values selected for these parameters depend on the nature of the strain being cultivated and on the geometry of the fermenter.

In practice the amplitude of the surge effect on the culture (which is explained below) is greater for talle columns (of the same cross-sectional area). Various tests have shown that this effect gives satisfactory results in practical terms when the ratio $H/S^2$ between the square of the height of any column and its cross-sectional area is greater than a value of the order of 12. The height will of course be selected to suit the strain of microorganisms so as not to subject them to excessive pressures.

The diagrams shown in FIGS. 4a, 4b, 4c and 4d illustrate the surge effects produced by the sequential infeed of air.

Figure 4A:
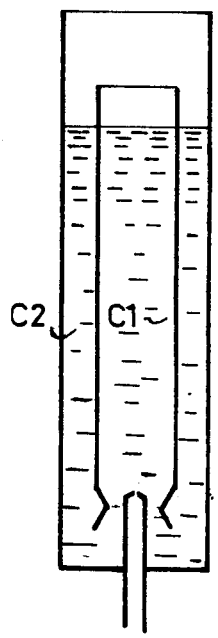

FIG. 4a represent the fermenter at the end of a non-injection period (state A shown in FIG. 3). By an intercommunicating vessel effect, the levels of the culture in columns $C_1$ and $C_2$ lie at substantially the same height.

Figure 4B:
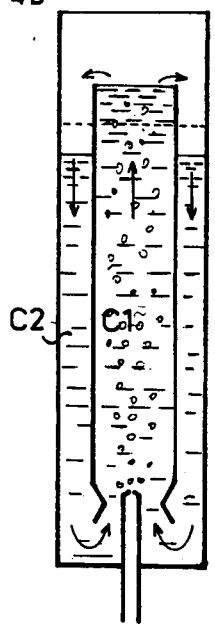

At each pulse, the injector emits into the container $C_1$ a volume of air which disperses in the form of a multitude of small bubbles (FIG. 4b, state B). The volume of culture contained in container $C_1$ increases owing to the arrival of these bubbles and the bubbles carry the liquid upwards. In addition the emission of air by the injector gives rise to a suction effect on the liquid at the base of the container $C_1$. These phenomena cause a rise in the level of liquid in container $C_1$ a fall in the level of liquid in container $C_2$ and cause a small amount of liquid to overflow from container $C_1$ into container $C_2$.

Figure 4C:
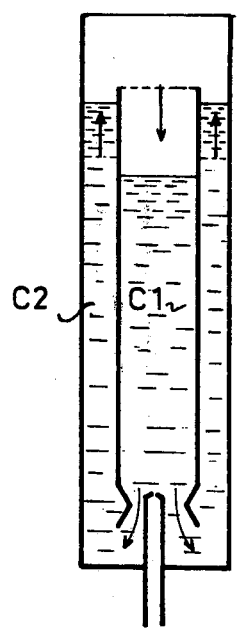

When the injection of air comes to an end (FIG. 4c, state C), the level of the culture in container $C_1$ drops suddenly and the level in container $C_2$ rises, with a certain amount of liquid crossing over from $C_1$ to $C_2$. Due to inertia the the levels in $C_1$ and $C_2$ go past the normal levels, as is shown by FIG. 4c.

Figure 4D:
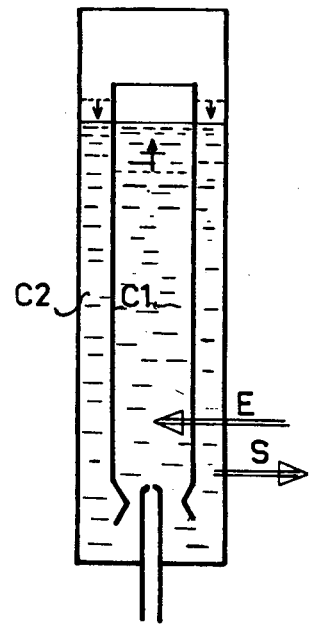

An oscillation occurs and the normal level, which is equal in the two containers, is able to establish itself by an intercommunicating vessel effect (FIG. 4d, state D). A new cycle can begin and this new cycle, as a result of air again being injected, will cause the level in $C_1$ to rise abruptly and the level in $C_2$ to fall abruptly. It is also possible to take advantage of the return oscillation to increase the amplitude of the surge by emitting a new pulse of air into $C_1$ before the liquid becomes completely motionless at the end of the previous cycle.

In this way, the culture has undergone on the one hand a pulsatory movement in the columns, which considerably assists in oxygenating and feeding the micro-organisms, and on the other hand a general movement as a result of flow from one column to the other. It should be noted that, in the course of the air injection, bubbles are drawn downward in container $C_2$ and travel down in the container with the liquid. When the injection stops, these bubbles rise again in the opposite direction and this movement considerably increases the efficiency with which the oxygen contained in the bubbles is used.

It should be mentioned that the fermenter may operate discontinuously if a predetermined quantity of seeded nutrient medium is placed in the columns $C_1$ and $C_2$ and if growth is allowed to continue for a predetermined time at the end of which the culture is extracted, the fermenter sterlised and a new charge introduced. It may equally well operate continuously if a predetermined amount of culture is tapped off after it has circulated completely and an identical amount of nutrient medium is injected. The injection may take place near the bottom of column $C_1$ (point E in FIG. 4d) and the extraction near the bottom of column $C_2$ (point S).

The curves in FIG. 5 demonstrate the effectiveness of the method of the invention as compared with the known airlift method.

Curve α shows the progress of the bacterial growth which has achieved in the course of experiments in a pilot fermenter of the kind shown in FIG. 1 but in which air was supplied continuously. Curve β shows the progress of the growth achieved using the method of the invention with alternating infeed.

The table below summarises the principal operating conditions in the two cases.

|  | Curve $v^\alpha$ (Conventional method) | Curve β (Method of the invention) |
| --- | --- | --- |
| Approximate height of column $C_1$ | 750 mm | 750 mm |
| Approximate height of column $C_2$ | 1000 mm | 1000 mm |
| Diameter of column $C_1$ | 93 mm | 93 mm |
| Diameter of column $C_2$ | 150 mm | 150 mm |
| Mean rate of air injection | 1 v.v.m | 1 v.v.m |
| Mode of injecting air | continuous | Sequential Frequency: 15 per min. Duration of each injection period 1 second. Throughput in injection period 4 v.v.m |
| Strain | Bacillus megaterium | Bacillus megaterium |
| Temperature | 30° C. | 30° C. |
| Growth rate in development phase | 0.192 hour$^{-1}$ | 0.245 hour$^{-1}$ |

For the same mean air consumption, it is found that the initial latency period is very much shorter in the case of curve β and that the rate of growth (gradient of the curve) is very much steeper in this case.

If the in-fermenter times are equal to 16 hours in both cases (total consumption of air identical) it is found that the method of the invention gives a culture whose concentration is equal to $1.4 \times 10^9$ micro-organisms per cm$^3$. The ratio between the concentrations is of order of 3:1.

To achieve an identical concentration with the conventional method, an in-fermenter time of the order of 21 hours would be necessary, which would result in a total air consumption approximately 31% greater than that for the method of the invention.

FIG. 6 shows another embodiment of fermenter. This fermenter is similar to the previous one and is supplied with air discontinuously but its inner column $C_1$ contains a plurality of perforated plates such as 9 distributed over its height. The function of these plates is on the one hand to break up the air bubbles at each level to prevent them from coalescing and on the other hand to increase the homogenisation and agitation of the culture under the prompting of the surges, which cause the culture to experience a backward and forward movement at the level of each plate.

In addition, the column $C_1$ is crowned at the top by a bell-shaped cowl 10 which is adapted to guide the air and cause it to mix in at the surface with the culture contained in column $C_2$. This improves the dissolution of oxygen in the culture.

FIG. 7 shows another embodiment in which an additional container $C_3$ is provided in parallel with container $C_2$ in such a way as to experience the surge effect jointly with the latter. The general flow of the culture is divided between container $C_2$ and container $C_3$. It should be mentioned that a plurality of containers such as $C_3$ could be arranged in parallel.

In this embodiment, container $C_3$ contains a filling 11 situated between two grids. This filling may be formed by a solid bed of bio-mass. The injections of substantially sterile air take place into container $C_1$ as before. Container $C_3$ may be aerated with bubbles of air which are injected discontinuously, as shown in FIG. 8b, during the periods when the main injections are stopped, by means of an ancillary electrically-operated valve 12 which is controlled by electrical means 4'. The length of the injections into container $C_3$ is shorter that the length of the injections into container $C_1$ to maintain the general flow of the liquid.

It is possible in this way to improve the aeration of container $C_3$ and to increase the surging by means of a short burst of air which takes place shortly after the end of each main injection into $C_1$. If reference is made to FIG. 4c, it will be realised that this boosts the rise in level in the secondary containers. This secondary injection could of course take place into column $C_2$ or any other column arranged in parallel. In the case of the fermenter shown in FIG. 1, it may be useful to make provision for such secondary injections of air when the oxygen requirements of strains are very great.

The invention is not of course restricted to the terms of the foregoing description and covers all modifications. In particular it is possible to use a plurality of fermenters in parallel, which are connected to a compressor which supplies them with air while changing over the periods of air injection.

What we claim is:

1. A method of gasifying and agitating a micro-organism culture to enable the growth of the culture to be accelerated, said culture being contained in a fermenter comprising at least two containers in communication with one another in their upper and lower regions, the method comprising injecting air in the form of bubbles at the base of one of the containers during injection periods of predetermined length, and stopping the air injection for establishing non-injection periods at a predetermined frequency alternating with said injection periods, so as to produce in the two containers a surging or pulsating effect on the culture and permit a general flow between the two containers.

2. A method according to claim 1, wherein the length of the said non-injection periods is of the order of 0.5 to 10 times the length of the injection periods. the injection frequency being equal to at least one per minute.

3. A method according to claim 1 or 2, wherein the injection frequency and the length of the injection periods are constant and are preset to suit the oxygen requirements of the micro-organisms and the amount of agitation required.

4. A method according to claim 1 or 2, wherein the injection frequency and the length of the injection periods are variable and are controlled by sensors associated with the culture for detecting its state and optimizing culture growth.

5. A method as in claim 1 and including injecting substantially sterile air into one of said containers near the intercommunication between the lower regions of the two containers for drawing the culture from the other of said containers into said one of said containers and thereby increase the surge effect in the culture.

6. A method according to claim 5, in which said one of said containers is a vertical column arranged in said other container, which comprises a vertical column of larger diameter, and wherein, each time the air is injected, culture overflows at the top of the first container into the second container, thus producing a general flow of culture between the two containers.

7. A method according to claim 1, wherein bubbles of substantially sterile air are injected discontinuously into the other of said containers during said non-injection periods, the length of the injections into the second container being less than the length of the injections into the first container.

* * * * *